US012605268B2

(12) United States Patent (10) Patent No.: US 12,605,268 B2

Ierulli (45) Date of Patent: Apr. 21, 2026

(54) MEDICAL DEVICE

(71) Applicant: HORIZON IP TECH, LLC, Honolulu, HI (US)

(72) Inventor: Joseph V. Ierulli, Sarasota, FL (US)

(73) Assignee: HORIZON IP TECH, LLC, Honolulu, HI (US)

( * ) Notice: Subject to any disclaimer, the term of this patent is extended or adjusted under 35 U.S.C. 154(b) by 671 days.

(21) Appl. No.: 17/736,284

(22) Filed: May 4, 2022

(65) Prior Publication Data

US 2022/0370229 A1 Nov. 24, 2022

Related U.S. Application Data

(60) Provisional application No. 63/201,692, filed on May 9, 2021.

(51) Int. Cl.
A61F 5/08 (2006.01)

(52) U.S. Cl.
CPC ..................................... A61F 5/08 (2013.01)

(58) Field of Classification Search
CPC .................................. A61F 5/08; A61F 13/02
See application file for complete search history.

(56) References Cited

U.S. PATENT DOCUMENTS

| | | | | | |
|---|---|---|---|---|---|
| 4,614,183 A | * | 9/1986 | McCracken | .......... | A61F 13/023 |
| | | | | | 602/57 |
| 4,619,654 A | * | 10/1986 | Abplanalp | ........ | A61F 13/00063 |
| | | | | | 604/890.1 |
| 5,653,224 A | * | 8/1997 | Johnson | ................. | A61F 13/023 |
| | | | | | 602/41 |
| 6,769,428 B2 | * | 8/2004 | Cronk | ................... | A61M 15/08 |
| | | | | | 606/199 |
| 2010/0228282 A1 | | 9/2010 | Fenton | | |
| 2011/0166594 A1 | * | 7/2011 | Eull | .......................... | A61F 5/08 |
| | | | | | 606/201 |
| 2016/0278967 A1 | * | 9/2016 | Ierulli | ....................... | A61F 5/08 |

FOREIGN PATENT DOCUMENTS

| | | |
|---|---|---|
| EP | 0051935 A2 | 5/1982 |
| EP | 0368541 A1 | 5/1990 |
| EP | 1683502 B1 | 2/2009 |
| WO | 2010039771 A1 | 4/2010 |

OTHER PUBLICATIONS

European Search Report of Feb. 3, 2023 for EP22171687.

* cited by examiner

*Primary Examiner* — Mohamed G Gabr
*Assistant Examiner* — Khoa Tan Le
(74) *Attorney, Agent, or Firm* — GrayRobinson, P.A.

(57) ABSTRACT

A medical device, comprising a plastic film and a support structure, wherein the plastic film, per se, has insufficient intrinsic stability to retain a planar shape against standard gravity, the support structure supports an area of the plastic film such that at least 80% of an entire area of the plastic film is inhibited from deforming, regardless of orientation, in response to standard gravity, and the support structure is manually inseparable from the plastic film.

8 Claims, 9 Drawing Sheets

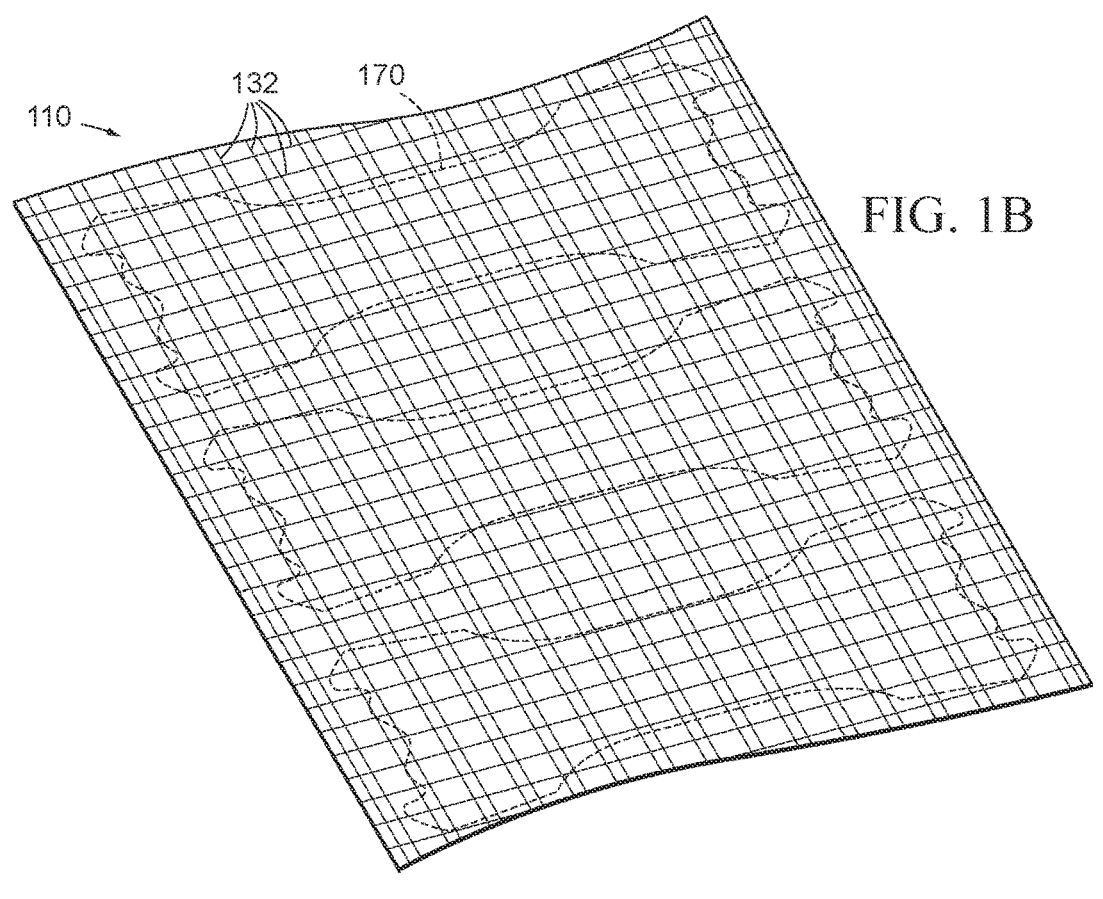
FIG. 1B
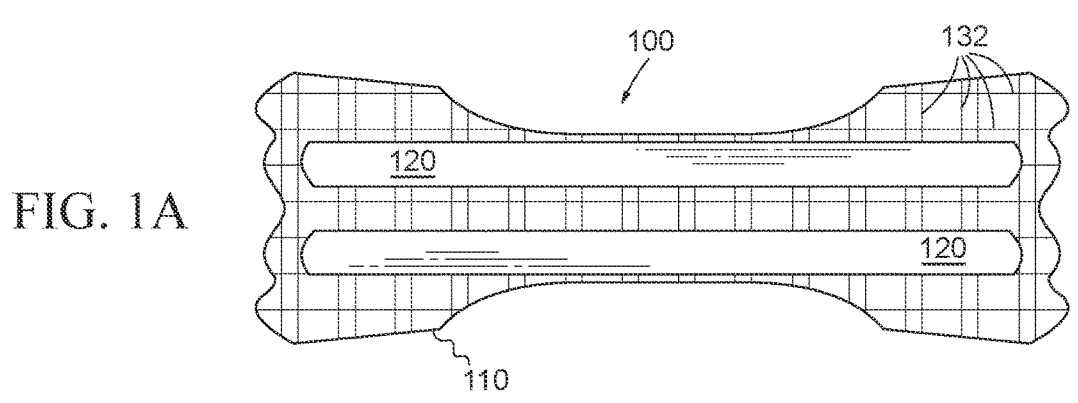
FIG. 1A
FIG. 1C
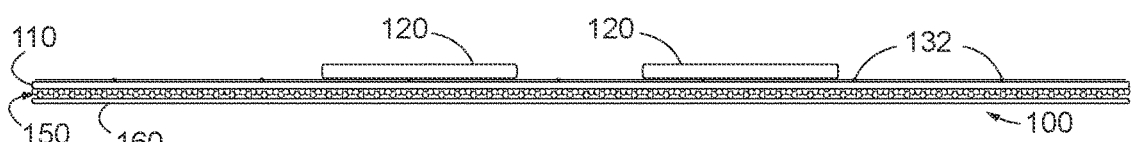

FIG. 6
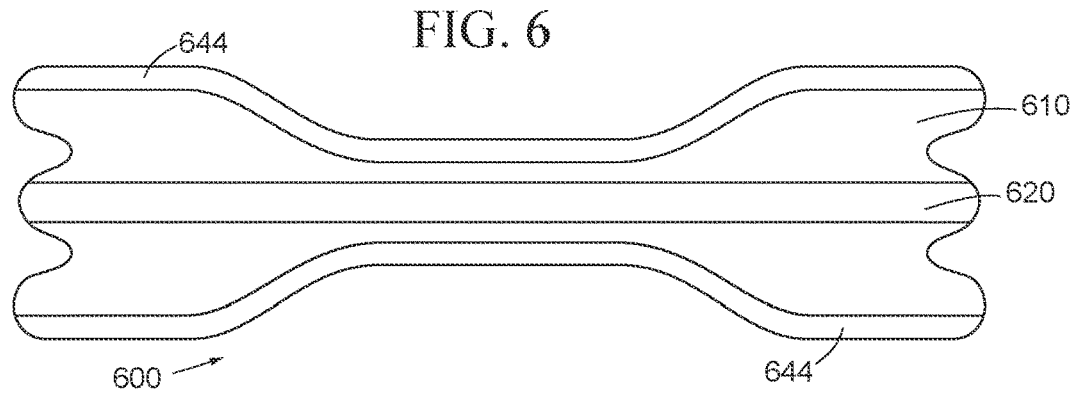
FIG. 7A
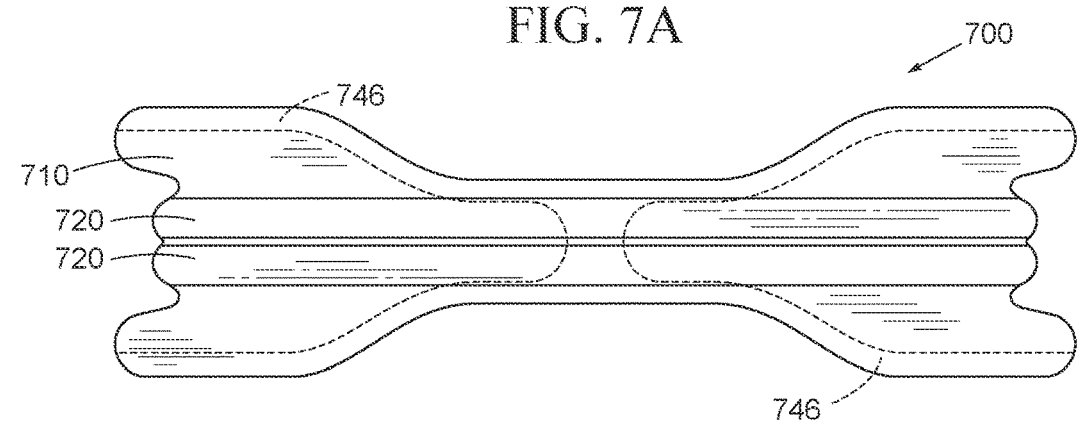
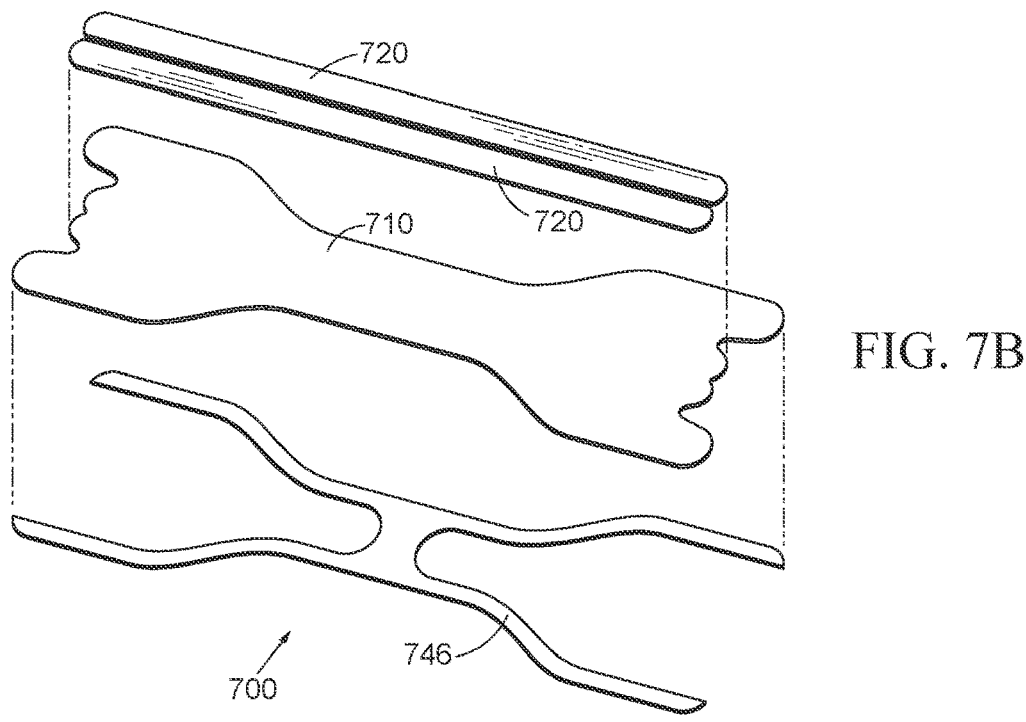
FIG. 7B

FIG. 10
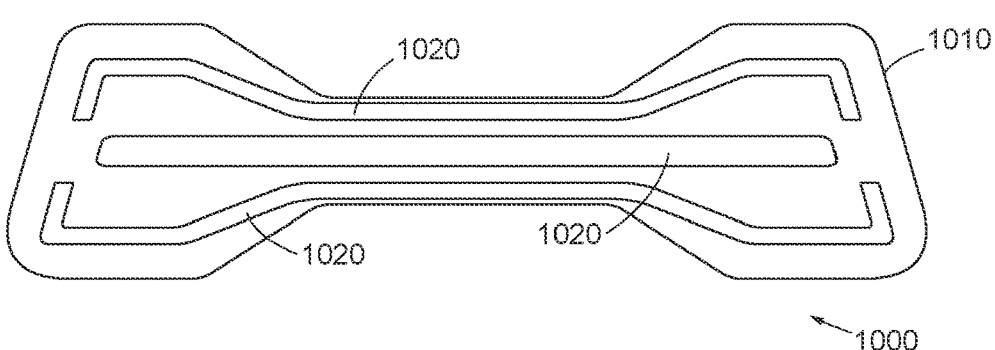
FIG. 11
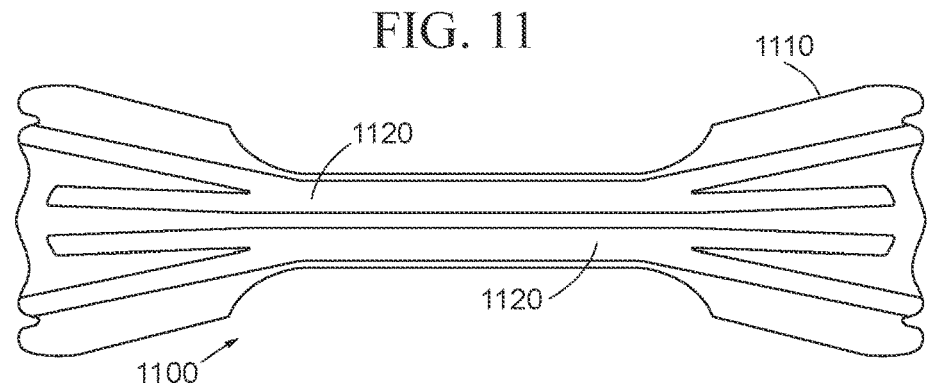
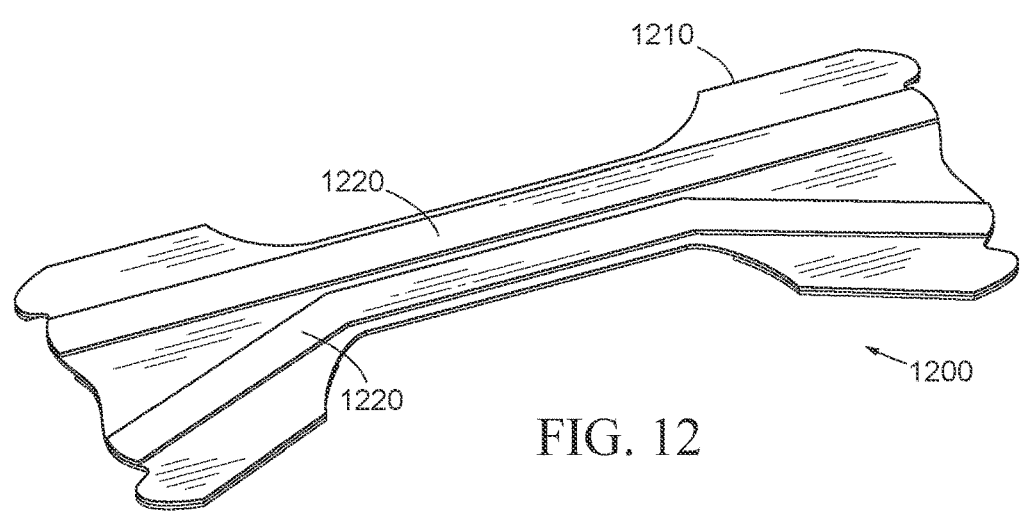
FIG. 12

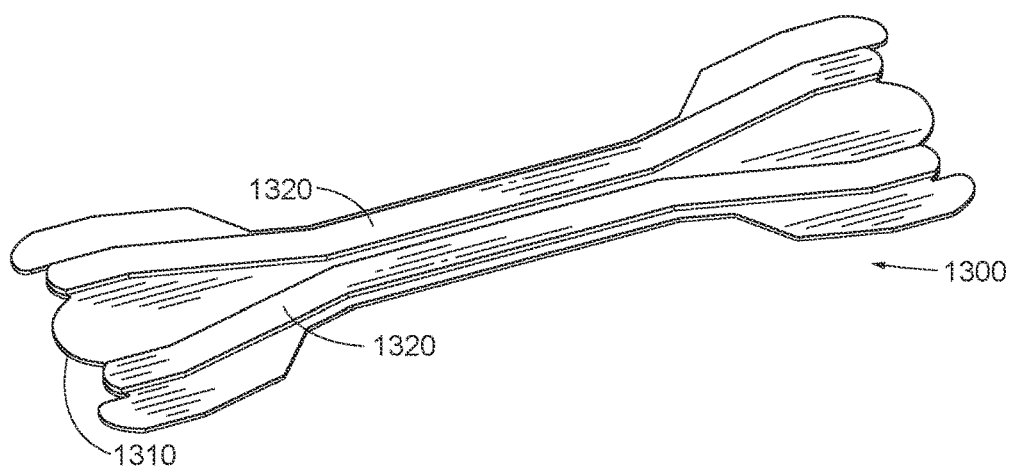
FIG. 14
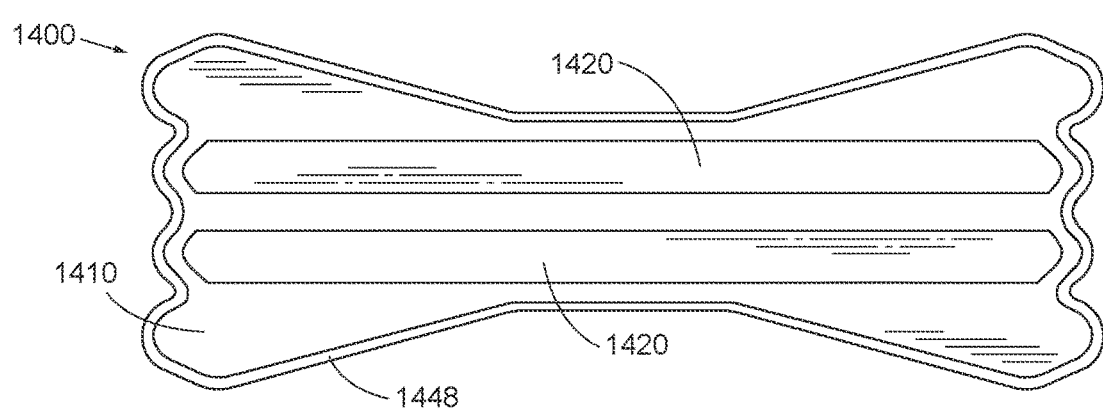
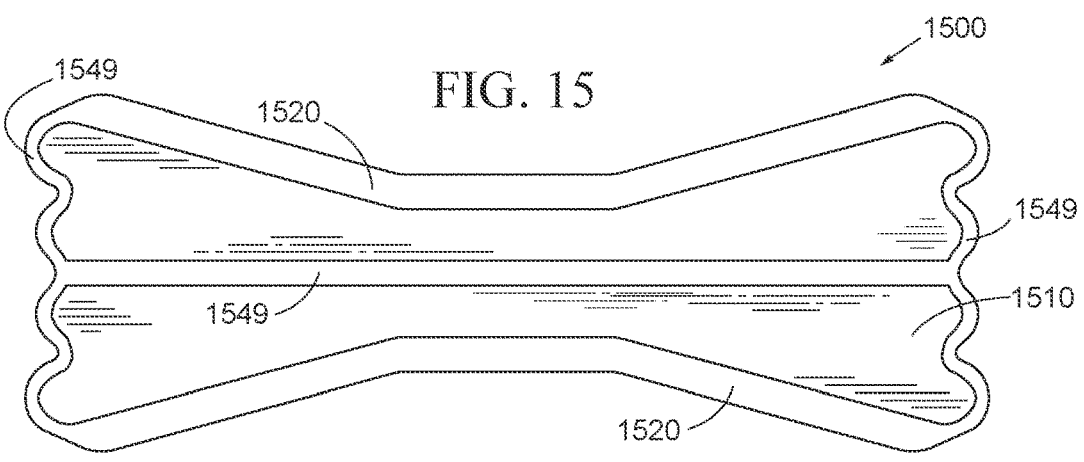
FIG. 15

MEDICAL DEVICE

CROSS-REFERENCE TO RELATED APPLICATIONS

This application claims priority under 35 U.S.C. § 119 to U.S. Provisional Application No. 63/201,692, filed on May 9, 2021, the entire disclosure of which is herein expressly incorporated by reference.

BACKGROUND OF THE DISCLOSURE

Field of the Disclosure

The present disclosure relates to a medical device as well as to a nasal dilator as well as to a method using a nasal dilator.

DESCRIPTION OF THE RELATED ART

A wide variety of medical devices such as bandages and nasal dilators are known.

The present disclosure expounds upon this background.

SUMMARY OF THE PRESENT DISCLOSURE

The aim of the present summary is to facilitate understanding of the present disclosure. The summary thus presents concepts and features of the present disclosure in a more simplified form and in looser terms than the detailed description below and should not be taken as limiting other portions of the present disclosure.

Loosely speaking, the present disclosure discloses a medical device comprising a plastic film and a support structure. The plastic film may be a flimsy plastic film that, for lack of intrinsic stability, droops during handling by a user, e.g. when the user is attempting to adhere the medical device to a person's skin. The support structure can inhibit such drooping by supporting at least a portion of the plastic film, thus making it easier for the user to accurately apply the medical device to a person's skin and/or preventing sections of the medical device from contacting other sections of the medical device, in particular adhesive sections, in a manner that could degrade the utility of the medical device. The support structure may be manually inseparable from the plastic film, which can ease overall handling of the medical device and prevent misuse that could degrade the utility of the medical device.

Loosely speaking, the present disclosure discloses a nasal dilator comprising a plastic film, at least one resilient member and tripartite release liner. The plastic film may be a flimsy plastic film that, for lack of intrinsic stability, droops during handling by a user, e.g. when the user is attempting to adhere the nasal dilator to their nose. The tripartite release liner can inhibit such drooping by retaining support for at least a portion of the plastic film during application to a user's nose, thus making it easier for the user to accurately apply the nasal dilator and/or preventing sections of the nasal dilator from contacting other sections of the nasal dilator, in particular adhesive sections, in a manner that could degrade the utility of the nasal dilator.

Other objects, advantages and embodiments of the present disclosure will become apparent from the detailed description below, especially when considered in conjunction with the accompanying drawings.

BRIEF DESCRIPTION OF THE DRAWINGS

The Figures show:

FIG. 1A a schematic depiction of a nasal dilator in accordance with the present disclosure.

FIG. 1B a schematic depiction of plastic film of the nasal dilator of FIG. 1A.

FIG. 1C a schematic depiction of an end edge view of nasal dilator 100 of FIG. 1A.

FIG. 6 a schematic depiction of a nasal dilator in accordance with the present disclosure.

FIG. 7A a schematic depiction of a nasal dilator in accordance with the present disclosure.

FIG. 7B an exploded view schematically depicting the nasal dilator of FIG. 7A.

FIG. 10 a schematic depiction of a nasal dilator in accordance with the present disclosure.

FIG. 11 a schematic depiction of a nasal dilator in accordance with the present disclosure.

FIG. 12 a schematic depiction of a nasal dilator in accordance with the present disclosure.

FIG. 13 a schematic depiction of a nasal dilator in accordance with the present disclosure.

FIG. 14 a schematic depiction of a nasal dilator in accordance with the present disclosure.

FIG. 15 a schematic depiction of a nasal dilator in accordance with the present disclosure.

DETAILED DESCRIPTION

Figure 1D:
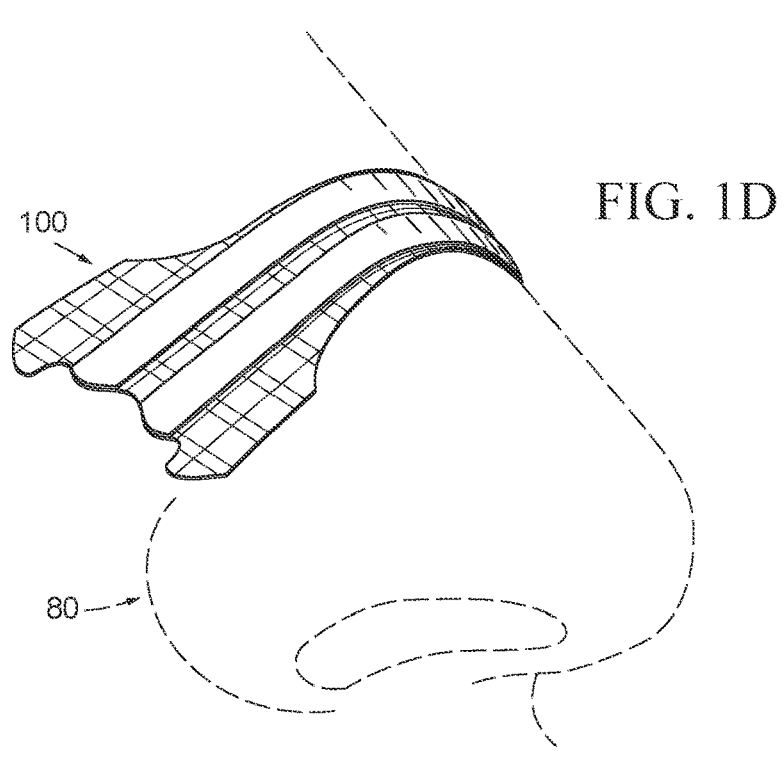
FIG. 1D a schematic depiction of the nasal dilator of FIG. 1A in use.

The various embodiments of the present disclosure and of the claimed invention, in terms of both structure and operation, will be best understood from the following detailed description, especially when considered in conjunction with the accompanying drawings.

Before elucidating the embodiments shown in the Figures, the various embodiments of the present disclosure will first be described in general terms.

The present disclosure discloses a medical device. The medical device may be a bandage, a wound care article, or a nasal dilator, in particular an external nasal dilator. The medical device may be a (thin, supple, or flexible) medical device, e.g. a medical device adhesively securable to human skin.

The medical device may comprise a plastic film. The plastic film may have a thickness of less than 0.1 mm, less than 0.05 mm, or less than 0.025 mm. The plastic film may be a medical grade and/or a biocompatible film. The plastic film may be a thermoplastic and/or polyurethane film. The plastic film may be a microporous film. The plastic film may comprise at least 20 pores, at least 50 pores or at least 100 pores per square centimeter. Each of the pores may have a respective maximum diameter of less than 2 μm, less than 5 μm, or less than 10 μm. The plastic film may be devoid of pores or openings having a diameter larger than 2 μm, 5 μm, or 10 μm. The plastic film may have a moisture vapor transmission rate of at least 200 grams, at least 400 grams, or at least 800 grams per square meter per 24 hours. The moisture vapor transmission rate may be determined by a standard test such as, for example, ASTM F1249, ASTM E96, or ASTM2622.

The medical device and/or plastic film may be dimensioned such that a maximum length along a longitudinal axis of the medical device/plastic film is not more than 10 times, not more than 5 times, or not more than 2 times a maximum width of the medical device/plastic film along a transverse axis perpendicular to the longitudinal axis. The medical device and/or plastic film may have a(n overall and/or general) shape of a quadrilateral, e.g. the shape of a rectangle, square, kite, parallelogram, trapezoid or rhombus. Similarly, the medical device and/or plastic film may have a(n overall and/or general) shape of an oval, circle, polygon, or star. Similarly, the medical device and/or plastic film may have a(n overall and/or general) shape of a dog-bone or barbell. In the present disclosure, a dog-bone or barbell shape may be understood as a shape consisting of two identical rectangles joined by a third rectangle, the three rectangles sharing a common axis of symmetry that constitutes a longitudinal axis of the dog-bone or barbell shape, the third rectangle having a width perpendicular to the longitudinal axis that is at least 10% or at least 20% less than a respective, individual width of the two identical rectangles perpendicular to the longitudinal axis. Similarly, the medical device and/or plastic film may have a(n overall and/or general) butterfly shape. In the present disclosure, a dog-butterfly shape may be understood as a shape consisting of two identical (isosceles) triangles joined by a rectangle, the rectangle having a width perpendicular to an axis of symmetry of the rectangle that extends from the one triangle to the other that is at least 10% or at least 20% less than a respective, individual width of the two triangles perpendicular to said axis of symmetry of the rectangle. The two triangles may share a common axis of symmetry with the rectangle. The shape need not be geometrically perfect, i.e. need not be a geometrically perfect rectangular, square, kite, circular, polygon, star, dog-bone, etc. The medical device and/or plastic film may be shaped such that an imaginary area of any one of the aforementioned shapes (rectangular, square, kite, circular, polygon, star, dog-bone, etc.) may be found such that not more than 15%, not more than 10% or not more than 5% of a total area of the medical device/plastic film does not overlap/coincide with the imaginary area, i.e. falls outside the imaginary area and/or is void, i.e. not present, within the bounds of the imaginary area. (An elucidation of the term "any" is given in the closing paragraphs of this specification.) The outermost peripheral edge of the plastic film may define an entire outermost peripheral edge of the medical device or at least 60%, at least 80%, or at least 90% of an entire outermost peripheral edge of the medical device.

The plastic film may be an elastic film. The plastic film may be capable of stretching elastically in response to a (dilating/stretching) force in the plane of the plastic film. The plastic film may inherently return to an initial, unbiased state in response to cessation of such a (dilating/stretching) force. The plastic film, per se, may have insufficient intrinsic stability to retain a(n overall) shape, e.g. at a macroscopic level (of observation) and/or in response to forces perpendicular to the plane of the plastic film. More specifically, the plastic film, per se, may have insufficient intrinsic stability to retain a(n overall) planar shape against (forces perpendicular to the plane of the plastic film arising from) standard gravity, e.g. an acceleration of 9.8 m/s². For example, the plastic film (per se) may be incapable of retaining a (macroscopically) planar shape in a cantilever arrangement in which the plastic film extends horizontally from a support by more than 4 mm or more than 8 mm. The plastic film (per se) may bend (as a result of its own mass) with a radius of curvature less than 2 mm, less than 1 mm or less than 0.5 mm when subjected to standard gravity, e.g. when the plastic film is in a cantilever arrangement (where a portion of the plastic film is supported and a remaining, extending portion is permitted to (freely) droop in response to gravity). In the present disclosure, the expression "per se" may be understood as meaning "in and of itself" or "on its own" or "by itself". As such, an "intrinsic stability of the plastic film, per se" may be understood as meaning an intrinsic stability (purely) of the plastic film itself, i.e. as if the plastic film were a homogeneous plastic film (devoid of any support structure).

The plastic film may comprise a first major surface and a second major surface. The first major surface of the plastic film may (be a surface configured to) face a user's skin during use. At least 10%, at least 20%, at least 50%, at least 80%, or at least 90% of the first major surface of the plastic film may be coated with a (biocompatible) adhesive, e.g. for (releasably) affixing the medical device to a user's skin. The adhesive may be a pressure-sensitive adhesive.

The medical device may comprise a support structure, e.g. a support structure that supports (an area of) the plastic film. The support structure may (visually and/or materially) distinct from the plastic film. Regardless of whether the support structure is (visually and/or materially) distinct from the plastic film, the support structure may be integrally formed with the plastic film and/or may be an integral component of the plastic film. The support structure may support (an area of) the plastic film such that the plastic film is inhibited from curling and/or folding against itself/against other portions of the medical device. The support structure may support (an area of) the plastic film such that an entire area of the plastic film or such that at least 60%, at least 80%, at least 90%, or at least 95% of an entire area of the plastic film is inhibited from (macroscopically) deforming. The area inhibited from deforming may be inhibited from deforming, e.g. bending (as a result of the mass of the plastic film) to a radius of curvature less than 5 mm, less than 10 mm or less than 20 mm when subjected to standard gravity. The ability of the support structure to inhibit such deforming of an entire area/a percentage of an entire area of the plastic film may be independent of an orientation (of the medical device). In other words, the support structure may inhibit such deforming regardless of an orientation (of the medical device). The support structure may comprise/consist of a plurality of components, e.g. a plurality of discrete components, a plurality of permanently joined components, a plurality of integrally-formed components, or a combination of discrete and/or permanently joined and/or integrally-formed components. The plurality of components may comprise, e.g. as described in further detail infra, any combination of components individually selected from the group consisting of a resilient member, a strut, a strip of (sheet-shaped) material, a support member and a fiber.

The support structure may be affixed to the first major surface of the plastic film. The support structure may be affixed to the second major surface of the plastic film. A first set of (components belonging to) the plurality of components (belonging to the support structure) may be affixed to the first major surface of the plastic film, and a second set of (components belonging to) the plurality of components (belonging to the support structure) may be affixed to the second major surface of the plastic film. The first and second sets may collectively constitute the plurality of components.

The support structure may be (manually) inseparable from the plastic film, e.g. in the sense that the support structure may be affixed to and/or integrated into the plastic film in a manner that inhibits and/or prevents the support structure from being (manually) separated from the plastic film (without incurring damage to the support structure and/or the plastic film, e.g. damage that would impair the function of the support structure and/or the plastic film). In the present specification, the term "manually" may be understood as meaning using (no other tool than) human hands.

The medical device may comprise a (sheet-like) release liner that covers the adhesive on the first major surface of the plastic film (prior to use). The release liner may be releasably adhered to the plastic film (via the adhesive). The release liner may be manually removable from the medical device, e.g. to expose the adhesive (immediately prior to affixing the medical device to a user's skin). The release liner may support (an area of) the plastic film such that the plastic film is inhibited from curling and/or folding against itself/against other portions of the medical device. The release liner may support (an area of) the plastic film such that an entire area of the plastic film or such that at least 60%, at least 80%, at least 90%, or at least 95% of an entire area of the plastic film is inhibited from (macroscopically) deforming. The area inhibited from deforming may be inhibited from deforming, e.g. bending (as a result of the mass of the plastic film) to a radius of curvature less than 5 mm, less than 10 mm or less than 20 mm when subjected to standard gravity. The ability of the release liner to inhibit such deforming of an entire area/a percentage of an entire area of the plastic film may be independent of an orientation (of the medical device). In other words, the release liner may inhibit such deforming regardless of an orientation (of the medical device). The release liner may comprise a substrate of a (Kraft) paper and/or a synthetic material, e.g. a plastic film. The substrate may be coated with a release agent, e.g. silicone, or other coating. The release liner may constitute an outermost component of the medical device.

The release liner may be a tripartite release liner. The tripartite release liner may consist of a first (liner) portion, a second (liner) portion, and an intermediate (liner) portion. The intermediate (liner) portion may be situated intermediate the first (liner) portion and the second (liner) portion. Each of the first (liner) portion, the second (liner) portion, and the intermediate (liner) portion may (respectively/individually) constitute not more than 40%, not more than 50%, or not more than 60% of a total (contact) area of the tripartite release liner. Each of the first (liner) portion, the second (liner) portion, and the intermediate (liner) portion may (respectively/individually) constitute not less than 20%, or not less than 30% of a total (contact) area of the tripartite release liner. In the present disclosure, the term "contact area" may be understood as the (overall) area of the regions in which the (tripartite) release liner contacts other elements of the medical device. In embodiments in which the plastic film defines the outer perimeter of the medical device and the (tripartite) release liner contacts an entirety of the first major surface of the plastic film, for example, the "contact area" may be the total area the plastic film. In embodiments in which the plastic film defines the outer perimeter of the medical device and the (tripartite) release liner contacts an entirety of an exposed portion of the first major surface of the plastic film as well as an entire surface of at least one resilient member affixed to the first major surface of the plastic film, for example, the "contact area" may likewise be the total area the plastic film. The intermediate (liner) portion may comprise a first tab and/or a second tab. The first tab may overlap the first (liner) portion, e.g. on a side of the first (liner) portion opposite the adhesive. The second tab may overlap the second (liner) portion, e.g. on a side of the first (liner) portion opposite the adhesive. Similarly, the first (liner) portion may comprise a third tab. The third tab may overlap the intermediate (liner) portion, e.g. on a side of the intermediate (liner) portion opposite the adhesive. Similarly, the second (liner) portion may comprise a fourth tab. The fourth tab may overlap the intermediate (liner) portion, e.g. on a side of the intermediate (liner) portion opposite the adhesive.

The medical device may comprise a (manually removable) cover liner. The cover liner may be (manually removably) affixed, e.g. via an adhesive, to an outermost (excepting the cover liner) surface of the medical device, e.g. to the second major surface of the plastic film. The cover liner may cover an entire area of the medical device/the plastic film or at least 60%, at least 80%, at least 90%, or at least 95% of an entire area of the medical device/the plastic film. The cover liner may comprise a sheet-like material such as (Kraft) paper and/or plastic film. Alternatively, the medical device may be devoid of (such) a cover liner. The cover liner may constitute an outermost component of the medical device, e.g. on a side of the medical device opposite the release liner. The second major surface of the plastic film may face the cover liner. The cover liner may be a carrier liner, e.g. a (so-called) carrier liner that provides support to the plastic film during (initial) manufacture and/or (subsequent) transport of the plastic film.

The medical device may be (manually) deformable, e.g. for the sake of affixing the medical device to an area of human skin (via the adhesive (on the first major surface of the plastic film)). Such deformation of the medical device may be a plastic deformation or an elastic deformation. As such, the deformation may comprise a bending (i.e. a plastic or elastic deformation) of the medical device or a (resilient) flexing (i.e. an elastic deformation) of the medical device. Deformation of the medical device to affix the medical device to an area of human skin may comprise bending an entirety of the medical device, e.g. such that an entire longitudinal axis of the medical device is bent, e.g. at a radius of curvature of at least 60 mm, at least 40 mm, or at least 20 mm. The medical device may (e.g. on account of an optional resiliency of the support structure, which support structure need not comprise a "resilient member" as described below to exhibit resilience) exert return forces in response to the deformation, e.g. return forces that, in the absence of other forces, would return the medical device to an undeformed/unbiased state. In a medical device devoid of a resilient member, e.g. in a bandage and wound care article, at least 60%, at least 80%, or at least 90% of the return forces may emanate from the support structure. In a medical device comprising a resilient member, e.g. in a nasal dilator, the return forces emanating from the resilient member(s) may constitute at least 80%, at least 90%, or at least 95% of the (overall) return forces emanating from the medical device. The adhesive (on the first major surface of the plastic film) may counteract the (overall) return forces (emanating from the medical device (as a whole)). Similarly, the (overall) return forces (emanating from the medical device (as a whole)) may be of insufficient magnitude to overcome adhesive forces of the adhesive affixing the medical device to the area of human skin. As such, the adhesive may retain the medical device on a user's skin despite deformation of the medical device (to conform to a shape of the user's skin (at a location where the medical device is affixed)).

Similarly, the support structure may be (manually) deformable, e.g. in response to (manual) forces perpendicular to a (major) planar surface (e.g. as described below) defined by the support structure. Such deformation of the support structure may be a plastic deformation or an elastic deformation. As such, the deformation may comprise a bending (i.e. a plastic or elastic deformation) of the support structure or a (resilient) flexing (i.e. an elastic deformation) of the support structure. For example, such deformation of the support structure may comprise bending the support structure such that a longitudinal axis of the support structure is bent. Deformation of the support structure to affix the medical device to an area of human skin may comprise bending (an entirety of) the support structure, e.g. such that a(n entire) longitudinal axis of the support structure is bent, e.g. at a radius of curvature of at least 60 mm, at least 40 mm, or at least 20 mm. The support structure may (e.g. on account of an optional resiliency of the support structure, which support structure need not comprise a "resilient member" as described below to exhibit resilience) exert return forces in response to the deformation, e.g. return forces that, in the absence of other forces, would return the support structure to an undeformed/unbiased state. The adhesive (on the first major surface of the plastic film) may counteract the return forces (emanating from the support structure). Similarly, the return forces (emanating from the support structure) may be of insufficient magnitude to overcome adhesive forces of the adhesive affixing the medical device to the area of human skin. As such, the adhesive may retain the medical device on a user's skin despite deformation of the medical device/the support structure (to conform to a shape of the user's skin (at a location where the medical device is affixed)). The support structure may exhibit rigidity and/or no (macroscopic) elasticity in response to (manual) forces parallel to a (major) planar surface (e.g. as described below) defined by the support structure.

The support structure (e.g. in an unbiased state) may define a (major) planar surface. More specifically, the support structure (e.g. in an unbiased state) may define a plurality of support regions (in planar arrangement) that define a (major) planar surface and/or correspond to regions of a (major) planar surface. The support regions may be regions (of the support structure) that contact and/or support the plastic film. The support regions may be distributed such that any contiguous region—defined by the intersection of a rectangular bounding box and an area bounded by an outermost perimeter of the plastic film and constituting 20% of the total area of the plastic film—is supported by/contacts not less than 10% or not less than 5% of a total area of the support regions.

Similarly, the support regions may be distributed such that any contiguous region—defined by the intersection of a rectangular bounding box and an area bounded by an outermost perimeter of the plastic film and constituting 10% of the total area of the plastic film—is supported by/contacts not less than 5% or not less than 2% of a total area of the support regions. The support structure may be a sheet-like structure. The support structure may have a(n overall) planar/sheet-like shape. The support structure may have a (maximum) thickness of less than 2 mm, less than 1 mm, or less than 0.5 mm (in a direction perpendicular to the defined (major) planar surface. For example, the support structure may fit between two imaginary parallel planes separated by 2 mm, 1 mm, or 0.5 mm.

The support structure may occupy less than 40%, less than 20%, less than 20%, less than 5%, or less than 2% of the entire area of the plastic film. More specifically, a total area occupied by the support structure, e.g. as viewed in a direction perpendicular to a major surface of the support structure and/or the plastic film, may be less than 40%, less than 20%, less than 20%, less than 5%, or less than 2% of the total area of the plastic film. Similarly, a total area occupied by the support regions of the support structure, e.g. as viewed in a direction perpendicular to a major surface of the support structure and/or the plastic film, may be less than 40%, less than 20%, less than 20%, less than 5%, or less than 2% of the total area of the plastic film.

The medical device may comprise at least one resilient member. In the present disclosure, the term "resilient member" may be understood as a component of the medical device configured to provide therapeutic function by stretching and/or dilating an anatomical structure of a user, e.g. a nasal passage. Additionally or alternatively, the term "resilient member" may be understood as a component of the medical device configured to be flexed over the bridge of a user's nose to dilate a nasal passage.

It should be noted that, in the nomenclature of the present disclosure, the at least one resilient member may constitute a (direct) sub-component of the medical device, per se, or may constitute a sub-sub-component of the medical device, namely a sub-component of the "support structure" sub-component of the medical device. In general, i.e. in all embodiments of a medical device in accordance with the present disclosure, the at least one resilient member may constitute a sub-component of the support structure, i.e. may constitute a tertiary (sub-sub-)level component of the medical device. Alternatively, in particular in embodiments of the medical device comprising a tripartite release liner, the at least one resilient member may constitute a sub-component of the medical device, per se, i.e. may constitute a secondary (sub-) level component of the medical device. As such, descriptions of embodiments comprising a tripartite release liner need not employ the "support structure" nomenclature in references to the at least one resilient member, i.e. may forsake the intermediate concept of a "support structure".

As touched upon above, the support structure may comprise the at least one resilient member. In other words, each of the at least one resilient member may constitute a corresponding component of the support structure. The support structure may comprise at least one support element, e.g. for supporting the plastic film in regions not sufficiently supported by the at least one resilient member. The support structure may consist of the at least one resilient member and the at least one support element. In the present disclosure, the term "resilient member" may be understood, additionally or alternatively to the previous descriptions, as a component of the support structure that (even in weakest arrangement) provides a supporting force several orders of magnitude larger, e.g. at least 1,000 or 10,000 times larger, than a minimal force necessary to inhibit an area of the plastic film (in horizontal, cantilever arrangement) from (macroscopically) deforming in response to standard gravity. Additionally or alternatively, the term "resilient member" may be understood as encompassing, exclusively or non-exclusively, a component of the support structure that (in weakest arrangement) exhibits that maximum stiffness of any component of the support structure. Additionally or alternatively, the term "resilient member" may be understood as a component of the support structure that (in weakest arrangement) exhibits a stiffness of at least 20%, at least 40%, at least 60% or at least 80% of a stiffness (in weakest arrangement) of a stiffest (in weakest arrangement) component of the support structure. In the present disclosure, the term "support element" may be understood as a component of the support structure that (in weakest arrangement) has a stiffness less than 1%, less than 5%, less than 10%, or less than 20% of a stiffness (in weakest arrangement) of a stiffest (in weakest arrangement) of the at least one resilient member. In the present disclosure, the term "stiffness" may be understood as a stiffness in response to a non-torsional force and/or in response to a force perpendicular to a major surface of the respective component of the support structure. For example, if a certain component of the support structure exhibits a minimum stiffness, A, in response to a force perpendicular to a major surface of the certain component and each of the at least one resilient member exhibits a respective, individual minimum stiffness, $B_n$, in response to a force perpendicular to a major surface of the respective, individual resilient member, then the certain component may be understood as constituting a support element if the minimum stiffness A is less than 1%, less than 5%, less than 10%, or less than 20% of the largest minimum stiffness $B_n$ respectively, individually exhibited by any one of the at least one resilient member.

As touched upon above, the support structure may comprise/consist of a plurality of fibers. Each fiber of the plurality of fibers may constitute a support element of the support structure. The plurality of fibers may comprise/consist of multi-strand fibers, single-strand fibers, or a combination of multi-strand and single-strand fibers. The plurality of fibers may comprise/consist of natural fibers, synthetic fibers, or a combination of natural and synthetic fibers. The plurality of fibers may comprise/consist of plastically deformable fibers, elastically deformable fibers, or a combination of plastically and elastically deformable fibers. The elastically deformable fibers may be (straight) fibers that strive to return to an initial/unbiased state in response to a deformation that bends a longitudinal axis of the respective fiber. For each fiber, an entire length of the respective fiber or at least 50% of an entire length of the respective fiber may constitute a support region of the support structure. The fibers may be arranged in crisscrossing arrangement. The fibers may be arranged in perpendicular arrangement. For example, a first set of fibers belonging to the plurality of fibers may be arranged in (straight or zigzag) parallel arrangement, i.e. with each individual fiber belonging to the first set being (straight/zigzag,) offset and parallel to each other fiber belonging to the first set, and a second set of fibers belonging to the plurality of fibers may be arranged in (straight or zigzag) parallel arrangement, i.e. with each individual fiber belonging to the second set being (straight/zigzag,) offset and parallel to each other fiber belonging to the second set, where (a respective overall longitudinal axis of) each individual fiber of the first set is perpendicular to (a respective overall longitudinal axis of) each individual fiber of the second set. Alternatively, the fibers may be arranged in skewed arrangement, e.g. at a skewing angle of not less than 45°, not less than 30° or not less than 20°. For example, a first set of fibers belonging to the plurality of fibers may be arranged in (straight or zigzag) parallel arrangement, i.e. with each individual fiber belonging to the first set being (straight/zigzag,) offset and parallel to each other fiber belonging to the first set, and a second set of fibers belonging to the plurality of fibers may be arranged in (straight or zigzag) parallel arrangement, i.e. with each individual fiber belonging to the second set being (straight/zigzag,) offset and parallel to each other fiber belonging to the second set, where (a respective overall longitudinal axis of) each individual fiber of the first set is skewed relative to (a respective overall longitudinal axis of) each individual fiber of the second set, e.g. at an angle of not less than 45°, not less than 30° or not less than 20°.

As touched upon above, the support structure may comprise at least one strut, e.g. a strut having an overall longitudinal axis perpendicular or oblique (by at least 45° or by at least 60°) to a longitudinal axis of any one of the at least one resilient member. The support structure may comprise at least one strut having an overall longitudinal axis parallel or oblique (by no more than 5° or by no more than 10°) to a longitudinal axis of any one of the at least one resilient member. The strut may have a length of less than 90%, or less than 95% of an edge-to-edge dimension of the medical device (as measured along an imaginary line coaxial to a longitudinal axis of the (respective) strut). Each longitudinal end of the strut may be distanced from an outermost peripheral edge of the medical device, e.g. by at least 5% or at least 10% of a length of the medical device (along a longitudinal axis of the medical device coaxial to a longitudinal axis of the (respective) strut). The strut may have a length of not less than 80%, not less than 90%, or not less than 95% of an edge-to-edge dimension of the medical device (as measured along an imaginary line coaxial to a longitudinal axis of the (respective) strut). The ends of the strut may coincide with respective edges of the medical device. The strut may be of a natural material, a synthetic material, or a combination of natural and synthetic materials. For example, the strut may comprise a thermoplastic resin, e.g. a (biaxially oriented) polyester resin such as (biaxially oriented) poly(ethylene terephthalate), often referred to by the abbreviation boPET/PET. The strut may be of the same material as the at least one resilient member. The strut may have a maximum thickness that is less than 20%, less than 10%, or less than 5% of a minimum thickness of the at least one resilient member. The strut may have a maximum width that is less than a minimum width of the at least one resilient member or less than 50% of the minimum width of the at least one resilient member.

At least 40%, at least 60%, or at least 80% of a major surface of the strut may be fastened, e.g. glued, to the plastic film. The strut may constitute a support element or a resilient element of the support structure.

As touched upon above, the support structure may comprise at least one strip of (sheet-shaped) material. The strip of material may be draped across (any of) the at least one resilient member, e.g. on a side of (any of) the at least one resilient member opposite the plastic film. A longitudinal axis of the strip of material may be within 45°, within 30°, or within 15° of perpendicular to a longitudinal axis of (any of) the at least one resilient member. The strip of material may be of a natural material, a synthetic material, or a combination of natural and synthetic materials. The strip of material may comprise a (sheet of) woven material and/or a film of material. The strip of material may be of the same material as the plastic film. The strip of material may have a width (perpendicular to a longitudinal axis of the strip of material and/or parallel to a longitudinal axis of the medical device) of at least 5% or at least 10% of a minimum length of the medical device. The strip of material may have a width of not more than 10% of not more than 20% of a minimum length of the medical device. The strip of material may have a length of not less than 80%, not less than 90%, or not less than 95% of a width of the medical device (along a transverse axis of the medical device coaxial to a longitudinal axis of the (respective) strip of material). The ends of the strip of material may coincide with respective edges of the medical device. At least 40%, at least 60%, or at least 80% of a major surface of the strip of material may be fastened, e.g. glued, to the plastic film. The strip of material may constitute a support element of the support structure.

As touched upon above, the support structure may comprise at least one support member that extends along a peripheral edge of the plastic film. Collectively, the at least one support member may extend along less than 80% or less than 90% of an entire peripheral edge of the plastic film. Collectively, the at least one support member may extend along at least 60%, at least 80%, or at least 90% of an entire peripheral edge of the plastic film. The support member may extend along an entirety of a peripheral edge of the plastic film. A first (portion of the) support member may extend along an entirety of a first longitudinal peripheral edge of the plastic film, and a second (portion of the) support member may extend along an entirety of a second longitudinal peripheral edge of the plastic film. The support member may have a length of less than 90%, or less than 95% of an edge-to-edge dimension of the medical device (as measured along an imaginary line coaxial to a longitudinal axis of the (respective) support member). Each longitudinal end of the support member may be distanced from an outermost peripheral edge of the medical device, e.g. by at least 5% or at least 10% of a length of the medical device (along a longitudinal axis of the medical device coaxial to a longitudinal axis of the (respective) support member). The support member may have a length of not less than 80%, not less than 90%, or not less than 95% of an edge-to-edge dimension of the medical device (as measured along an imaginary line coaxial to a longitudinal axis of the (respective) strut). The ends of the support member may coincide with respective edges of the medical device. The support member may be of a natural material, a synthetic material, or a combination of natural and synthetic materials. For example, the support member may comprise a thermoplastic resin, e.g. a (biaxially oriented) polyester resin such as (biaxially oriented) poly(ethylene terephthalate), often referred to by the abbreviation boPET/PET. The support member may be of the same material as the at least one resilient member. The support member may have a maximum thickness that is less than 20%, less than 10%, or less than 5% of a minimum thickness of the at least one resilient member. The support member may have a maximum width that is less than a minimum width of the at least one resilient member or less than 50% of the minimum width of the at least one resilient member. The at least one support member may be integrally formed with the at least one resilient member. An entirety or at least a portion of a peripheral edge of the at least one support member may coincide with a corresponding entirety/portion of a peripheral edge of the plastic film or the medical device. Similarly, an entirety or at least a portion of a peripheral edge of the at least one support member may be inwardly offset (by less than 10% or less than 5% of a maximum width of the plastic film (perpendicular to a longitudinal axis of the plastic film))

from a corresponding portion of a peripheral edge of the plastic film or the medical device.

The at least one support member may comprise at least one C-shaped support member. A first C-shaped support member may extend along (a first portion of) a first longitudinal peripheral edge of the plastic film, along (an entirety of) a (first transverse) peripheral edge of the plastic film intermediate the first longitudinal peripheral edge and a second longitudinal peripheral edge of the plastic film, and along (a first portion of) the second longitudinal peripheral edge. The first portion of the first/second longitudinal peripheral edge may constitute less than 40%, less than 30%, or less than 20% of the first/second longitudinal peripheral edge. A second C-shaped support member may extend along (a second portion of) the first longitudinal peripheral edge of the plastic film, along (an entirety of) a (second transverse) peripheral edge of the plastic film intermediate the first longitudinal peripheral edge and the second longitudinal peripheral edge, and along (a second portion of) the second longitudinal peripheral edge. The second portion of the first/second longitudinal peripheral edge may constitute less than 40%, less than 30%, or less than 20% of the first/second longitudinal peripheral edge. An overall longitudinal axis of the first/second transverse peripheral edge may be perpendicular or oblique (by at least 45° or by at least 60°) to a(n overall) longitudinal axis of the plastic film.

As touched upon above, the medical device/support structure may comprise at least one resilient member. For example, the medical device/support structure may comprise one, two or three resilient member(s). The resilient member may be of a natural material, a synthetic material, or a combination of natural and synthetic materials. For example, the resilient member may comprise a thermoplastic resin, e.g. a (biaxially oriented) polyester resin such as (biaxially oriented) poly(ethylene terephthalate), often referred to by the abbreviation boPET/PET. The resilient member may have a thickness (in a direction perpendicular to a major surface of the resilient member) in the range of 0.05 mm to 1 mm, e.g. in the range of 0.1 mm to 0.5 mm. The resilient member may have a width of not less than 10%, not less than 20%, or not less than 30% of a minimum width of the medical device (perpendicular to a longitudinal axis of the medical device). The resilient member may have a width of not more than 30%, not more than 40%, or not more than 50% of a minimum width of the medical device (perpendicular to a longitudinal axis of the medical device). The resilient member may have a length (along a longitudinal axis of the medical device coaxial to a longitudinal axis of the (respective) resilient member) of less than 90%, or less than 95% of a length of the medical device (along a longitudinal axis of the medical device coaxial to a longitudinal axis of the (respective) resilient member). Each longitudinal end of the resilient member may be distanced from an outermost peripheral edge of the medical device, e.g. by at least 5% or at least 10% of a length of the medical device (along a longitudinal axis of the medical device coaxial to a longitudinal axis of the (respective) resilient member). The resilient member may have a length of not less than 80%, not less than 90%, or not less than 95% of a length of the medical device (along a longitudinal axis of the medical device coaxial to a longitudinal axis of the (respective) resilient member). The ends of the resilient member may coincide with respective edges of the medical device. End regions of the resilient member may be forked. A longitudinal axis of any one of the at least one resilient member may be parallel or oblique (by no more than 5° or by no more than 10°) to a longitudinal axis of any other of the at least one resilient member. Each of the at least one resilient member may comprise a first major surface and a second major surface. Any of the at least one resilient member may exhibit rigidity and/or no (macroscopic) elasticity in response to (manual) forces parallel to the first/second major surface. Any of the at least one resilient member may be (manually) deformable. Any of the at least one resilient member may be (manually) deformable in response to (manual) forces perpendicular to the first/second major surface. Such deformation of the respective resilient member may comprise resiliently flexing the respective resilient member such that a longitudinal axis of the respective resilient member is bent. The at least one resilient member may be deformed as a result of an affixing of the medical device to an area of human skin, e.g. as described above. Particularly in the case of a(n external) nasal dilator, the at least one resilient member may be deformed as a result of a (resilient) flexing of the medical device/nasal dilator over a bridge of a (user's) nose, i.e. as a result of a (resilient) flexing of the medical device/nasal dilator to at least partially conform to a contour of the bridge of the (user's) nose. More specifically, the at least one resilient member may be deformed as a result of an affixing of the medical device/nasal dilator to a user's nostrils across a bridge of a (user's) nose. The at least one resilient member may exert return forces in response to the deformation, e.g. return forces that, in the absence of other forces, would return the at least one resilient member to an undeformed/unbiased state. The return forces emanating from the at least one resilient member, e.g. in in response to a deformation of the at least one resilient member resulting from an affixing of the medical device/nasal dilator to a user's nostrils across a bridge of a nose, may (be sufficient to) dilate a nasal passage of the (user's) nose.

The medical device may comprise a(n absorbent) pad, e.g. a pad of a soft (relative to human skin) and/or absorbent material such as cotton gauze or cotton. The pad may be affixed to (a central region of) the first major surface of the plastic film. The pad may occupy at least 20%, at least 40% or at least 60% of a total area of the plastic film. The pad may occupy not more than 20%, not more than 40% or not more than 60% of a total area of the plastic film. The pad may be distanced from an outermost peripheral edge of the plastic film, e.g. such that (every point along) an outermost peripheral edge of the pad is distanced from a closest point belonging to the outermost peripheral edge of the plastic film (by at least 5% or at least 10% of minimum width of the plastic film, or by at least 5% or at least 10% of a dimension of the plastic film along a straight line joining the respective two points). Similarly, the pad may be distanced from an outermost peripheral edge of the plastic film, e.g. such that, for every diameter across the plastic film, an outermost peripheral edge of the pad is distanced from a closest point belonging to the outermost peripheral edge of the plastic film by at least 5% or at least 10% of a dimension of the plastic film along the respective diameter.

The present disclosure furthermore discloses a method using a nasal dilator, e.g. a nasal dilator as disclosed supra comprising a tripartite release liner.

The method may comprise manually removing the intermediate portion of the tripartite release liner from the plastic film, e.g. to expose an intermediate portion of the adhesive coating on an intermediate region of the first major surface of the plastic film. The method may comprise affixing the intermediate region to the bridge of a user's nose via the exposed intermediate portion of the adhesive coating, Similarly, the method may comprise manually removing the first portion of the tripartite release liner from the plastic film, e.g. to expose a first portion of the adhesive coating on a first region of the first major surface of the plastic film. The method may comprise affixing the first region to the bridge of a user's nose via the exposed first portion of the adhesive coating.

Similarly, the method may comprise manually removing the second portion of the tripartite release liner from the plastic film, e.g. to expose a second portion of the adhesive coating on a second region of the first major surface of the plastic film. The method may comprise affixing the second region to the bridge of a user's nose via the exposed second portion of the adhesive coating.

The step of removing the intermediate portion of the tripartite release liner from the plastic film may be effected after the steps of removing the first portion of the tripartite release liner from the plastic film and affixing the first region to the bridge of a user's nose. Similarly, the step of removing the intermediate portion of the tripartite release liner from the plastic film may be effected after the steps of removing the second portion of the tripartite release liner from the plastic film and affixing the second region to the bridge of a user's nose.

The step of removing the first portion of the tripartite release liner from the plastic film may be effected after the steps of removing the intermediate portion of the tripartite release liner from the plastic film and affixing the intermediate region to the bridge of a user's nose. Similarly, the step of removing the first portion of the tripartite release liner from the plastic film may be effected after the steps of removing the second portion of the tripartite release liner from the plastic film and affixing the second region to the bridge of a user's nose.

The step of removing the second portion of the tripartite release liner from the plastic film may be effected after the steps of removing the intermediate portion of the tripartite release liner from the plastic film and affixing the intermediate region to the bridge of a user's nose. Similarly, the step of removing the second portion of the tripartite release liner from the plastic film may be effected after the steps of removing the first portion of the tripartite release liner from the plastic film and affixing the first region to the bridge of a user's nose.

The various embodiments of the present disclosure having been described above in general terms, the embodiments shown in the Figures will now be elucidated.

FIG. 1A schematically depicts a nasal dilator 100 in accordance with the present disclosure, e.g. as described above. In the illustrated embodiment, nasal dilator 100 comprises a dog-bone shaped plastic film 110 and a support structure. The support structure comprises two resilient members 120 and a plurality of fibers 132.

FIG. 1B schematically depicts plastic film 110 of nasal dilator 100 of FIG. 1A prior to a cutting of plastic film 132 along what then becomes a perimeter 170 of nasal dilator 100.

FIG. 1C schematically depicts an end edge view of nasal dilator 100 of FIG. 1A. In the illustrated embodiment, a first major surface of plastic film 110 is coated with an adhesive 150. A manually removable release liner 160 covers adhesive 150. The two resilient members 120 and the plurality of fibers 132 are affixed to a second major surface of plastic film 110.

FIG. 1D schematically depicts nasal dilator 100 of FIG. 1A in use, i.e. flexed over the bridge of and removably adhesively affixed to a user's nose 80.

Figure 2A:
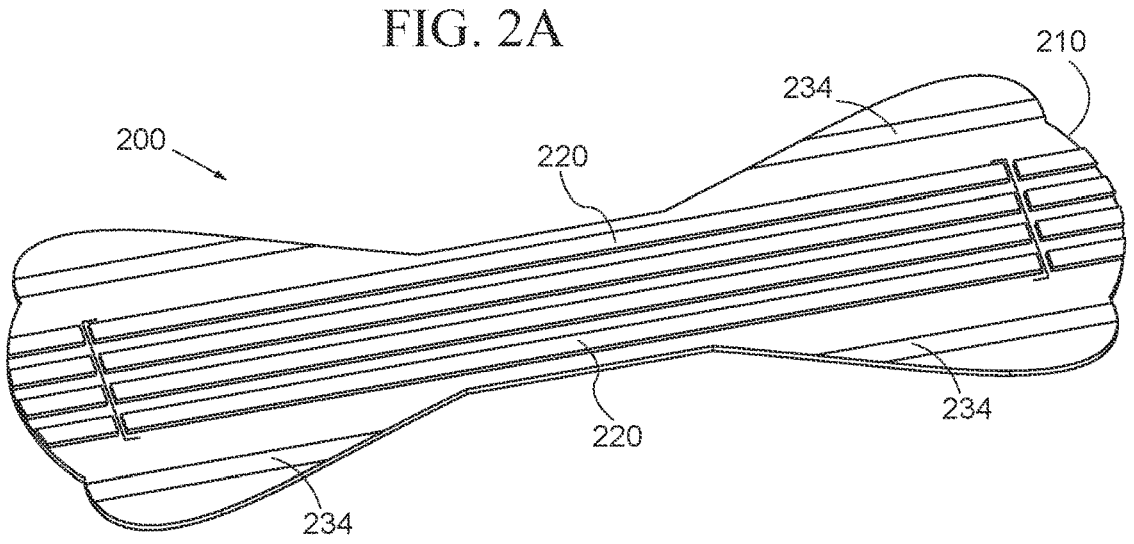
FIG. 2A a schematic depiction of a nasal dilator in accordance with the present disclosure.

FIG. 2A schematically depicts a nasal dilator 200 in accordance with the present disclosure, e.g. as described above. In the illustrated embodiment, nasal dilator 200 comprises a butterfly-shaped plastic film 210 and a support structure. The support structure comprises three resilient members 220 and a plurality of struts 234. A respective longitudinal axis of the individual struts 234 is parallel to a respective longitudinal axis of the individual resilient members 220.

Figure 2B:
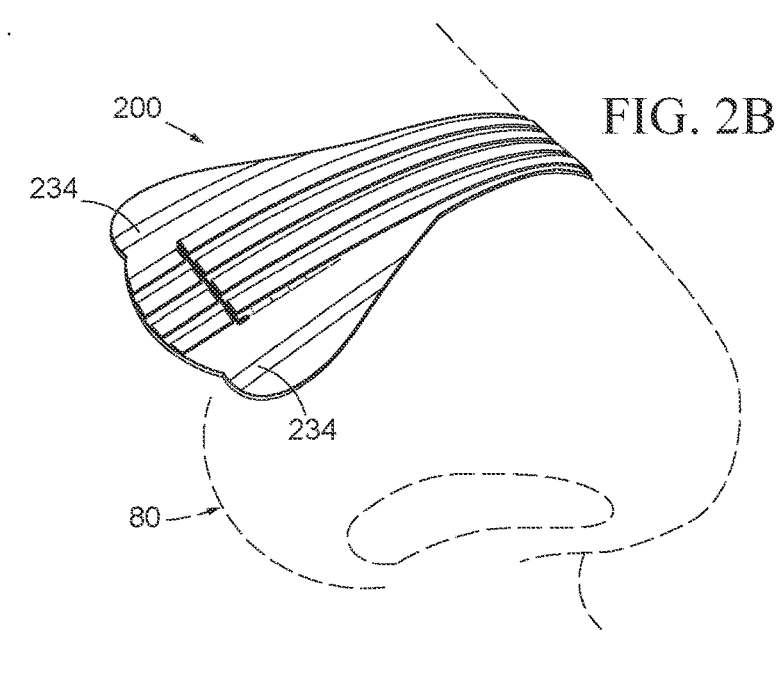
FIG. 2B a schematic depiction of the nasal dilator of FIG. 2A in use.

FIG. 2B schematically depicts nasal dilator 200 of FIG. 2A in use, i.e. flexed over the bridge of and removably adhesively affixed to a user's nose 80.

Figure 2C:
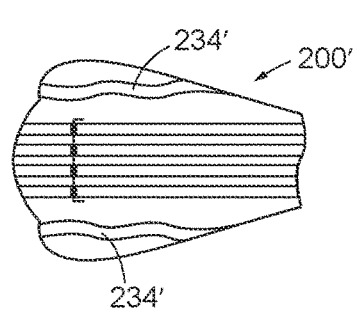
FIG. 2C a schematic depiction of another nasal dilator in accordance with the present disclosure.

FIG. 2C schematically depicts a nasal dilator 200' that is identical to nasal dilator 200 of FIG. 2A except that struts 234' have a wavy shape as opposed to straight struts 234 of FIG. 2A.

Figure 3:
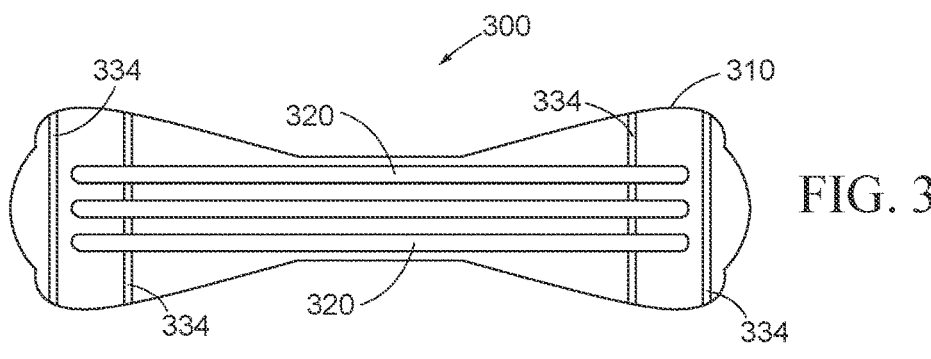
FIG. 3 a schematic depiction of a nasal dilator in accordance with the present disclosure.

FIG. 3 schematically depicts a nasal dilator 300 in accordance with the present disclosure, e.g. as described above. In the illustrated embodiment, nasal dilator 300 comprises a butterfly-shaped plastic film 310 and a support structure. The support structure comprises three resilient members 320 and a plurality of struts 334. A respective longitudinal axis of the individual struts 334 is perpendicular to a respective longitudinal axis of the individual resilient members 320.

Figure 4:
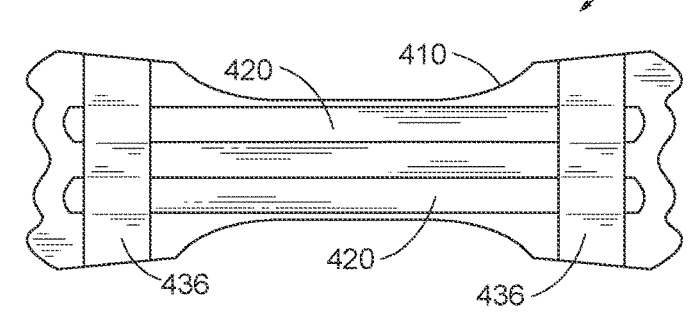
FIG. 4 a schematic depiction of a nasal dilator in accordance with the present disclosure.

FIG. 4 schematically depicts a nasal dilator 400 in accordance with the present disclosure, e.g. as described above. In the illustrated embodiment, nasal dilator 400 comprises a dog-bone shaped plastic film 410 and a support structure. The support structure comprises two resilient members 420 and two strips of material 436. The strips of material 436 are draped across resilient members 420 on a side of resilient members 420 opposite the plastic film. A respective longitudinal axis of the individual strips of material 436 is perpendicular to a respective longitudinal axis of the individual resilient members 420.

Figure 5A:
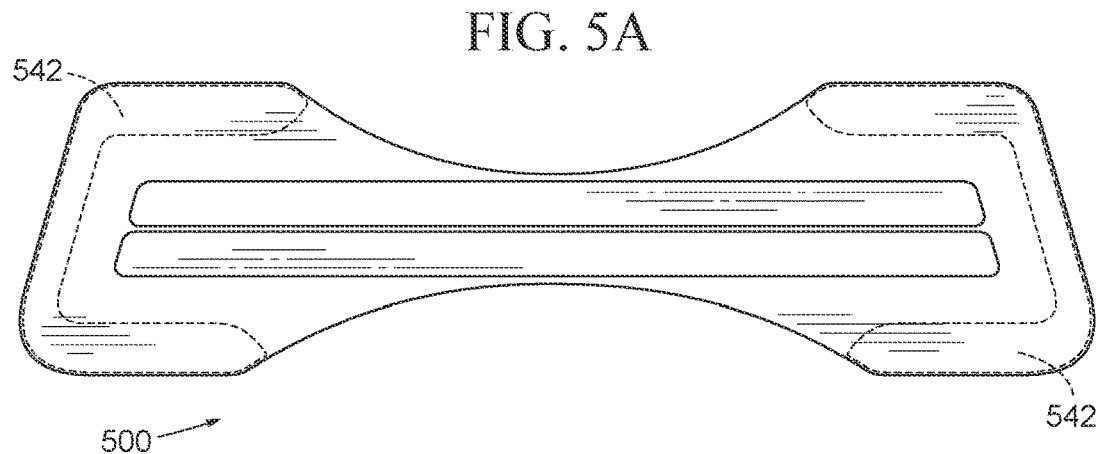
FIG. 5A a schematic depiction of a nasal dilator in accordance with the present disclosure.

FIG. 5A schematically depicts a nasal dilator 500 in accordance with the present disclosure, e.g. as described above. In the illustrated embodiment, nasal dilator 500 comprises a generally dog-bone shaped plastic film 510 and a support structure. The support structure comprises two resilient members 520 and two C-shaped support members 542. Each of C-shaped support members 542 extends along respective portion of a peripheral edge of plastic film 510.

Figure 5B:
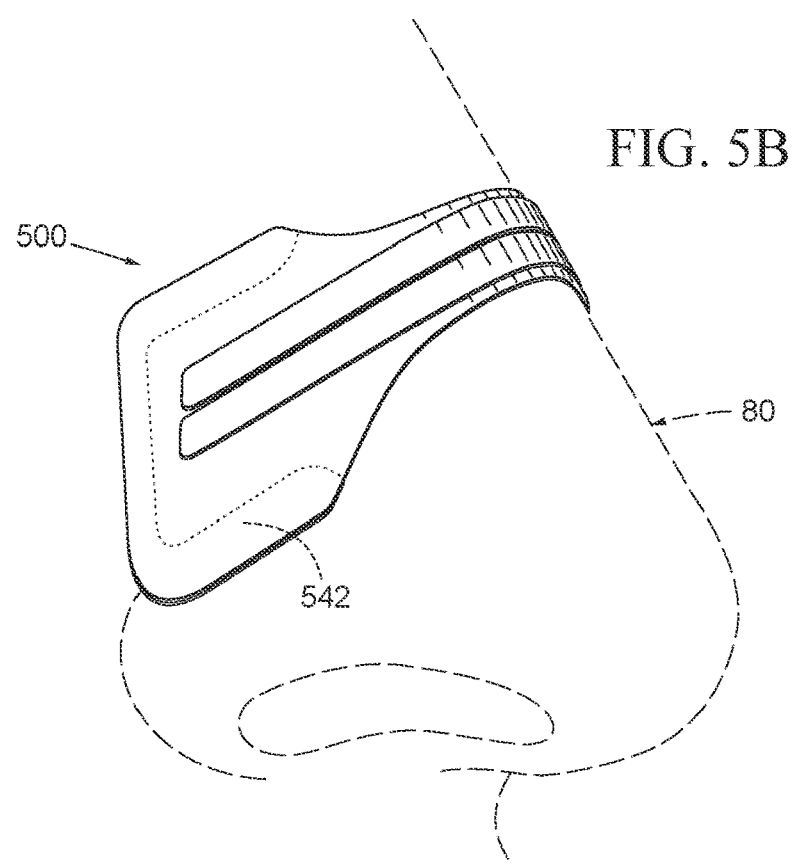
FIG. 5B a schematic depiction of the nasal dilator of FIG. 5A in use.

FIG. 5B schematically depicts nasal dilator 500 of FIG. 5A in use, i.e. flexed over the bridge of and removably adhesively affixed to a user's nose 80.

FIG. 6 schematically depicts a nasal dilator 600 in accordance with the present disclosure, e.g. as described above. In the illustrated embodiment, nasal dilator 600 comprises a dog-bone shaped plastic film 610 and a support structure. The support structure comprises a resilient member 620 and two support members 644. Each of support members 644 extends along an entirety of a respective longitudinal peripheral edge of plastic film 610.

FIG. 7A schematically depicts a nasal dilator 700 in accordance with the present disclosure, e.g. as described above. In the illustrated embodiment, nasal dilator 700 comprises a dog-bone shaped plastic film 710 and a support structure. The support structure comprises two resilient members 720 and a support member 746. A first portion of support member 746 extends along a first longitudinal peripheral edge of plastic film 710, and a second portion of support member 746 extends along a second longitudinal peripheral edge of plastic film 710. Support member 746 is affixed to a first major surface of plastic film 710, and resilient members 720 are affixed to a second major surface of plastic film 710.

FIG. 7B is an exploded view schematically depicting nasal dilator 700 of FIG. 7A.

Figure 8A:
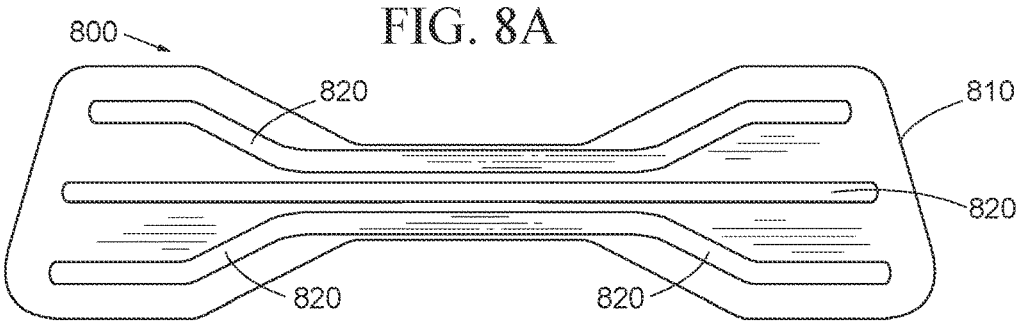
FIG. 8A a schematic depiction of a nasal dilator in accordance with the present disclosure.

FIG. 8A schematically depicts a nasal dilator 800 in accordance with the present disclosure, e.g. as described above. In the illustrated embodiment, nasal dilator 800 comprises a dog-bone shaped plastic film 810 and three resilient members 820. Each resilient member 820 has a length of less than 95% of a length of nasal dilator 800 along a longitudinal axis of nasal dilator 800 coaxial to a longitudinal axis of the (respective) resilient member 820.

Figure 8B:
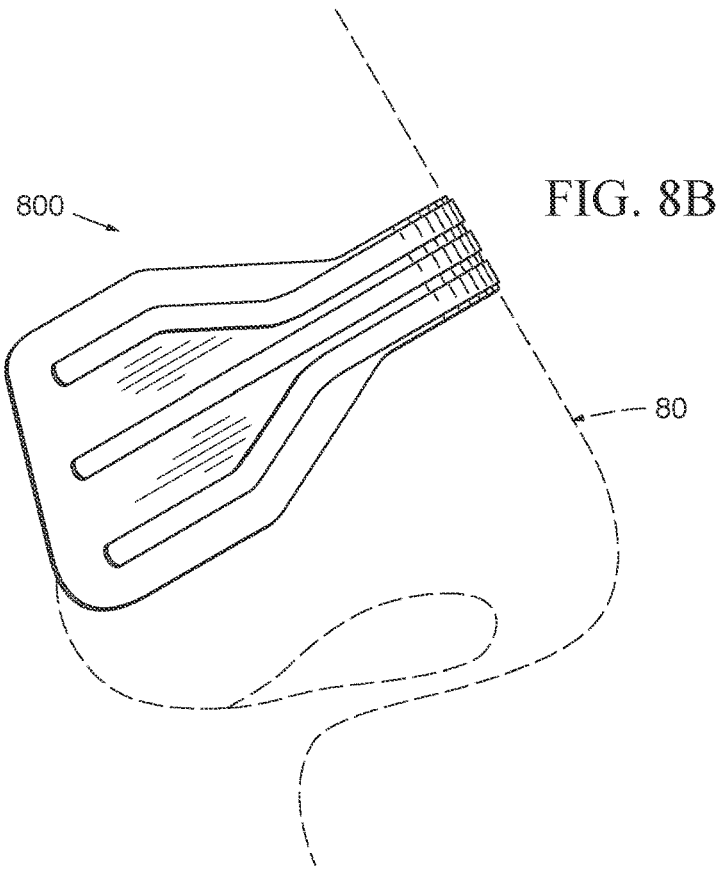
FIG. 8B a schematic depiction of the nasal dilator of FIG. 8B in use.

FIG. 8B schematically depicts nasal dilator 800 of FIG. 8B in use, i.e. flexed over the bridge of and removably adhesively affixed to a user's nose 80.

Figure 9:
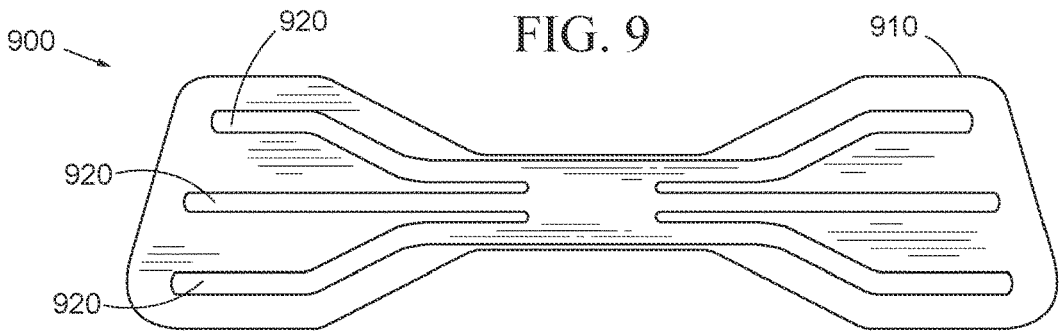
FIG. 9 a schematic depiction of a nasal dilator in accordance with the present disclosure.

FIG. 9 schematically depicts a nasal dilator 900 in accordance with the present disclosure, e.g. as described above. In the illustrated embodiment, nasal dilator 900 comprises a dog-bone shaped plastic film 910 and three resilient members 920. The three resilient members 920 are joined and form an integral element. Each resilient member 920 has a length of less than 95% of a length of nasal dilator 900 along a longitudinal axis of nasal dilator 900 coaxial to a longitudinal axis of the (respective) resilient member 920.

FIG. 10 schematically depicts a nasal dilator 1000 in accordance with the present disclosure, e.g. as described above. In the illustrated embodiment, nasal dilator 1000 comprises a dog-bone shaped plastic film 1010 and three resilient members 1020. Each resilient member 1020 has a length of less than 95% of a length of nasal dilator 1000 along a longitudinal axis of nasal dilator 1000 coaxial to a longitudinal axis of the (respective) resilient member 1020.

FIG. 11 schematically depicts a nasal dilator 1100 in accordance with the present disclosure, e.g. as described above. In the illustrated embodiment, nasal dilator 1100 comprises a butterfly-shaped shaped plastic film 1110 and two resilient members 1120. Resilient members 1120 have forked end regions.

FIG. 12 schematically depicts a nasal dilator 1200 in accordance with the present disclosure, e.g. as described above. In the illustrated embodiment, nasal dilator 1200 comprises a dog-bone shaped plastic film 1210 and two resilient members 1220. Resilient members 1220 differ from one another in shape.

FIG. 13 schematically depicts a nasal dilator 1300 in accordance with the present disclosure, e.g. as described above. In the illustrated embodiment, nasal dilator 1300 comprises a dog-bone shaped plastic film 1310 and two resilient members 1320.

FIG. 14 schematically depicts a nasal dilator 1400 in accordance with the present disclosure, e.g. as described above. In the illustrated embodiment, nasal dilator 1400 comprises a dog-bone shaped plastic film 1410 and a support structure. The support structure comprises two resilient members 1420 and a support member 1448. Support member 1448 extends around an entire periphery of plastic film 1410. Resilient members 1420 are distinct from support member 1448.

FIG. 15 schematically depicts a nasal dilator 1500 in accordance with the present disclosure, e.g. as described above. In the illustrated embodiment, nasal dilator 1500 comprises a dog-bone shaped plastic film 1510 and a support structure. The support structure comprises two resilient members 1520 and a plurality of support members 1549. Resilient members 1520 and support members 1549 are integrally formed, i.e. form an integral element. Collectively, resilient members 1520 and support members 1549 extend around an entire periphery of plastic film 1510.

Figures 16A, 16B:
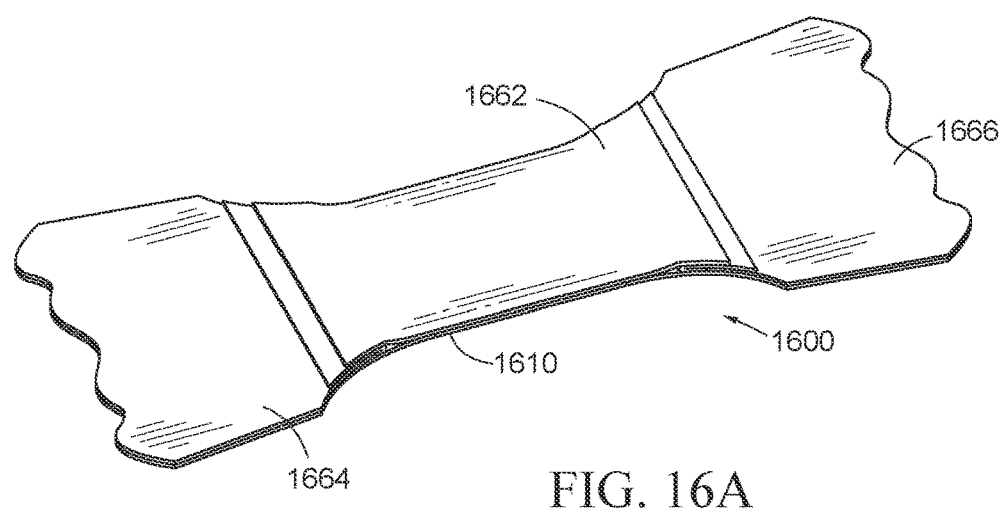
FIG. 16A a schematic depiction of a nasal dilator in accordance with the present disclosure.
FIG. 16B an exploded view schematically depicting the nasal dilator of FIG. 16A.

FIG. 16A schematically depicts a nasal dilator 1600 in accordance with the present disclosure, e.g. as described above. FIG. 16B is an exploded view schematically depicting nasal dilator 1600 of FIG. 16A. In the illustrated embodiment, nasal dilator 1600 comprises a dog-bone shaped plastic film 1610, two resilient members 1620 and a tripartite release liner. Tripartite release liner comprises an intermediate potion 1662, a first portion 1664 and second portion 1666.

In the present disclosure, the verb "may" is used to designate optionality/noncompulsoriness. In other words, something that "may" can, but need not. In the present disclosure, the verb "comprise" may be understood in the sense of including. Accordingly, the verb "comprise" does not exclude the presence of other elements/actions. In the present disclosure, relational terms such as "first," "second," "top," "bottom" and the like may be used solely to distinguish one entity or action from another entity or action without necessarily requiring or implying any actual such relationship or order between such entities or actions.

In the present disclosure, the term "any" may be understood as designating any number of the respective elements, e.g. as designating one, at least one, at least two, each or all of the respective elements. Similarly, the term "any" may be understood as designating any collection(s) of the respective elements, e.g. as designating one or more collections of the respective elements, wherein a (respective) collection may comprise one, at least one, at least two, each or all of the respective elements. The respective collections need not comprise the same number of elements.

In the present disclosure, the expression "at least one" is used to designate any (integer) number or range of (integer) numbers (that is technically reasonable in the given context). As such, the expression "at least one" may, inter cilia, be understood as one, two, three, four, five, ten, fifteen, twenty or one hundred. Similarly, the expression "at least one" may, inter cilia, be understood as "one or more," "two or more" or "five or more."

In the present disclosure, expressions in parentheses may be understood as being optional. As used in the present disclosure, quotation marks may emphasize that the expression in quotation marks may also be understood in a figurative sense. As used in the present disclosure, quotation marks may identify a particular expression under discussion.

In the present disclosure, many features are described as being optional, e.g. through the use of the verb "may" or the use of parentheses. For the sake of brevity and legibility, the present disclosure does not explicitly recite each and every combination and/or permutation that may be obtained by choosing from the set of optional features. However, the present disclosure is to be interpreted as explicitly disclosing all such combinations/permutations. For example, a system described as having three optional features may be embodied in seven different ways, namely with just one of the three possible features, with any two of the three possible features or with all three of the three possible features.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of the invention, even those disclosed solely in combination with other features of the invention, may be combined in any configuration excepting those readily apparent to the person skilled in the art as nonsensical. Likewise, use of the singular and plural is solely for the sake of illustration and is not to be interpreted as limiting. Except where the contrary is explicitly noted, the plural may be replaced by the singular and vice-versa.

The above disclosure may be summarized as comprising the following embodiments.

Embodiment 1

A medical device, comprising:

a plastic film; and a support structure, wherein said plastic film, per se, has insufficient intrinsic stability to retain a planar shape against standard gravity, said support structure supports an area of said plastic film such that at least 80% of an entire area of said plastic film is inhibited from deforming, regardless of orientation, in response to standard gravity, and said support structure is manually inseparable from said plastic film.

Embodiment 2

The medical device of Embodiment 1, wherein:

at least 10% of a major surface of said plastic film is coated with an adhesive, and return forces emanating from said support structure in response to a deformation of said support structure resulting from an affixing of said medical device, via said adhesive, to an area of human skin such that an entirety of said support structure is bent—bending a longitudinal axis of said support structure—at a radius of curvature of 40 mm are of insufficient magnitude to overcome adhesive forces of said adhesive affixing said medical device to said area of human skin.

Embodiment 3

The medical device of Embodiment 1 or 2, wherein:

said support structure occupies not more than a first given percentage of said entire area of said plastic film, where said first given percentage is selected from the group consisting of 5%, 10%, 20% and 40%.

Embodiment 4

The medical device of any one of the preceding Embodiments, wherein:

said support structure comprises a plurality of fibers in crisscrossing arrangement.

Embodiment 5

The medical device of any one of the preceding Embodiments, wherein:

said support structure defines a plurality of support regions, in planar arrangement, that support said plastic film.

Embodiment 6

The medical device of any one of the preceding Embodiments, wherein:
    said support structure defines a plurality of distributed support regions, in planar arrangement, that support said plastic film.

Embodiment 7

The medical device of any one of the preceding Embodiments, wherein:
    said plastic film has a moisture vapor transmission rate of at least 200 grams per square meter per 24 hours.

Embodiment 8

The medical device of any one of the preceding Embodiments, wherein:
    said plastic film has a thickness of less than 0.025 mm.

Embodiment 9

The medical device of any one of the preceding Embodiments, wherein:
    said medical device is an external nasal dilator, and said support structure comprises at least one resilient member, wherein
    return forces emanating from said at least one resilient member in response to a deformation of said at least one resilient member resulting from an affixing of said external nasal dilator to a user's nostrils across a bridge of a nose dilate a nasal passage of said nose.

Embodiment 10

The medical device of Embodiment 9, wherein:
    said support structure comprises at least one support element.

Embodiment 11

The medical device of Embodiment 10, wherein:
    each of said at least one support element has a respective stiffness that is less than a second given percentage of a stiffness of a stiffest of said at least one resilient member, where said second given percentage is selected from the group consisting of 5%, 10% and 20%.

Embodiment 12

The medical device of Embodiment 10 or 11, wherein:
    each of said at least one support element is individually selected from the group consisting of:
        a strut having an overall longitudinal axis perpendicular to a longitudinal axis of any one of said at least one resilient member;
        a strut having an overall longitudinal axis parallel to a longitudinal axis of any one of said at least one resilient member;
        a strut having an overall longitudinal axis oblique to a longitudinal axis of any one of said at least one resilient member;
        a strip of material draped across said at least one resilient member opposite said plastic film, a longitudinal axis of said strip of material being within 45° of perpendicular to a longitudinal axis of said at least one resilient member;
        a support member that extends along a peripheral edge of said plastic film;
        a support member that extends along an entirety of a peripheral edge of said plastic film;
        a support member that extends along an entirety of a longitudinal peripheral edge of said plastic film; and
        a C-shaped support member that extends along a first longitudinal peripheral edge of said plastic film, along a peripheral edge of said plastic film intermediate said first longitudinal peripheral edge and a second longitudinal peripheral edge of said plastic film, and along said second longitudinal peripheral edge.

Embodiment 13:

An external nasal dilator, comprising:
    a plastic film;
    at least one resilient member; and
    a tripartite release liner, wherein
    said plastic film, per se, has insufficient intrinsic stability to retain a planar shape against standard gravity,
    at least 10% of a major surface of said plastic film is coated with an adhesive,
    said tripartite release liner is releasably adhered to said plastic film via said adhesive and supports at least a portion of said plastic film such that at least 60% of said plastic film is inhibited from deforming, regardless of orientation, in response to standard gravity, and
    said tripartite release liner is manually separable from said plastic film.

Embodiment 14

The external nasal dilator of Embodiment 13, wherein:
    said tripartite release liner consists of a first portion, a second portion, and an intermediate portion,
    each of said first portion, said second portion, and said intermediate portion individually constituting not more than 50% of a total area of said tripartite release liner.

Embodiment 15

The external nasal dilator of Embodiment 13 or 14, wherein:
    said plastic film has a moisture vapor transmission rate of at least 200 grams per square meter per 24 hours.

Embodiment 16

The external nasal dilator of any one of Embodiments 13-15, wherein:
    said plastic film has a thickness of less than 0.025 mm.

Embodiment 17

The external nasal dilator of any one of Embodiments 13-16, wherein:
    return forces emanating from said at least one resilient member in response to a deformation of said at least one resilient member resulting from an affixing of said external nasal dilator to a user's nostrils across a bridge of a nose dilate said nostrils.

Embodiment 18:

A method using an external nasal dilator, wherein:
said external nasal dilator comprises:
a plastic film;
at least one resilient member; and
a tripartite release liner, wherein
said tripartite release liner consists of a first portion, a second portion, and an intermediate portion,
said plastic film, per se, has insufficient intrinsic stability to retain a planar shape against standard gravity,
at least 10% of a major surface of said plastic film comprises an adhesive coating, and
said tripartite release liner is releasably adhered to said plastic film via said adhesive coating and supports at least a portion of said plastic film such that at least 60% of said plastic film is inhibited from deforming, regardless of orientation, in response to standard gravity,
said method comprising:
manually removing said intermediate portion from said plastic film to expose an intermediate portion of said adhesive coating on an intermediate region of said major surface,
affixing said intermediate region to a bridge of a user's nose via said exposed intermediate portion of said adhesive coating,
manually removing said first portion from said plastic film to expose a first portion of said adhesive coating on a first region of said major surface,
affixing said first region to a first nostril of a user's nose via said exposed first portion of said adhesive coating,
manually removing said second portion from said plastic film to expose a second portion of said adhesive coating on a second region of said major surface, and
affixing said second region to a second nostril of a user's nose via said exposed second portion of said adhesive coating.

Embodiment 19

The method of Embodiment 18, wherein:
said plastic film has a thickness of less than 0.025 mm,
said plastic film has a moisture vapor transmission rate of at least 200 grams per square meter per 24 hours, and
return forces emanating from said at least one resilient member in response to a deformation of said at least one resilient member collectively resulting from said affixing of said intermediate portion, said affixing of said first portion and affixing of said second portion dilate said first nostril and said second nostril.

Embodiment 20

The method of Embodiment 18 or 19, wherein:
each of said first portion, said second portion, and said intermediate portion individually constitutes not more than 50% of a total area of said tripartite release liner.

The invention claimed is:

1. An external nasal dilator comprising:
a plastic film having insufficient intrinsic stability to retain a planar shape against standard gravity;
a support structure that supports an area of said plastic film such that at least 80% of an entire area of said plastic film is inhibited from deforming, regardless of orientation, in response to standard gravity;
said support structure being manually inseparable from said plastic film;
said support structure including a resilient member that dilates nasal passages of a user's nose when the external nasal dilator is adhered to the user's nose; and
said support structure including a support element that supports said plastic film in areas not supported by the resilient member and inhibits said plastic film from deforming therein, the support element having a plurality of fibers in crisscrossing arrangement and a stiffness that is less than 20% of a stiffness of the resilient member.

2. The external nasal dilator of claim 1, wherein:
at least 10% of a major surface of said plastic film is coated with an adhesive for affixing the plastic film to the user's nose.

3. The external nasal dilator of claim 1, wherein said support structure occupies not more than a first given percentage of said entire area of said plastic film, where said first given percentage is selected from the group consisting of 5%, 10%, 20% and 40%.

4. The external nasal dilator of claim 1, wherein said plurality of fibers in crisscrossing arrangement extend along a first longitudinal peripheral edge of said plastic film, along a peripheral edge of said plastic film intermediate said first longitudinal peripheral edge and a second longitudinal peripheral edge of said plastic film, and along said second longitudinal peripheral edge.

5. The external nasal dilator of claim 1, wherein said support structure defines a plurality of support regions, in planar arrangement, that support said plastic film.

6. The external nasal dilator of claim 1, wherein said support structure defines a plurality of distributed support regions, in planar arrangement, that support said plastic film.

7. The external nasal dilator of claim 1, wherein said plastic film has a moisture vapor transmission rate of at least 200 grams per square meter per 24 hours.

8. The external nasal dilator of claim 1, wherein said plastic film has a thickness of less than 0.025 mm.

* * * * *